(12) United States Patent
Des Clers

(10) Patent No.: US 7,005,991 B1
(45) Date of Patent: Feb. 28, 2006

(54) METHOD FOR ANTICIPATING, DELAYING AND/OR PREVENTING THE RISK OF SPONTANEOUS COMBUSTION AND/OR EXPLOSION OF AN EXPLOSIVE ATMOSPHERE

(76) Inventor: Bertrand Des Clers, 9 quai Malaquais, F-75006 Paris (FR)

( * ) Notice: Subject to any disclaimer, the term of this patent is extended or adjusted under 35 U.S.C. 154(b) by 0 days.

(21) Appl. No.: 10/009,126

(22) PCT Filed: May 5, 2000

(86) PCT No.: PCT/EP00/04414

§ 371 (c)(1),
(2), (4) Date: Nov. 7, 2001

(87) PCT Pub. No.: WO00/68684

PCT Pub. Date: Nov. 16, 2000

(30) Foreign Application Priority Data

May 7, 1999 (DE) ................................ 099 00 332

(51) Int. Cl.
 *G08B 17/00* (2006.01)
(52) U.S. Cl. ...................... 340/588; 340/591; 340/506; 340/521; 340/628; 340/632
(58) Field of Classification Search ................ 340/588, 340/501, 591, 601, 618, 632, 628, 506, 521; 73/25.01, 23.25, 35.14, 35.15, 35.17; 703/1.01, 703/1.06, 1.07, 25, 35, 37
See application file for complete search history.

(56) References Cited

U.S. PATENT DOCUMENTS

| 4,549,815 A | | 10/1985 | Venkat et al. |
| 5,159,839 A | * | 11/1992 | Silber et al. .................. 73/714 |
| 5,255,553 A | * | 10/1993 | Hale et al. .................... 73/19.1 |
| 5,886,625 A | * | 3/1999 | Uto et al. ................. 340/450.2 |
| 5,904,190 A | * | 5/1999 | Patel .......................... 141/198 |

FOREIGN PATENT DOCUMENTS

| GB | 394736 | 7/1933 |
| JP | 9-304310 | 11/1997 |
| WO | WO89/08253 | 9/1989 |
| WO | WO98/18001 | 4/1998 |

OTHER PUBLICATIONS

Directive 1999/92/EC, *J. European Communities*, L23/57-L23/64 (Jan. 2000).

* cited by examiner

*Primary Examiner*—Hung Nguyen
(74) *Attorney, Agent, or Firm*—Merchant & Gould P.C.

(57) ABSTRACT

The invention concerns a method for anticipating and/or delaying and/or preventing the risk of spontaneous combustion and/or explosion of an explosive atmosphere preserved in a confined or semi-confined medium, which consists in measuring the temperature of the mixing from the moment said mixture has been created and determining the critical moment of spontaneous combustion and/or explosion of said atmosphere by determining the unexpired inducting period, on the basis of the time which has elapsed between the creation of said atmosphere and the critical moment beyond which there is a risk of spontaneous combustion and/or explosion of said atmosphere.

2 Claims, 3 Drawing Sheets

METHOD FOR ANTICIPATING, DELAYING AND/OR PREVENTING THE RISK OF SPONTANEOUS COMBUSTION AND/OR EXPLOSION OF AN EXPLOSIVE ATMOSPHERE

SUBJECT OF THE INVENTION

The present invention relates to a process for anticipating, delaying and/or preventing the risk of spontaneous ignition and/or explosion, under atmospheric conditions, of an explosive atmosphere, that is to say of a mixture of air with flammable substances in the form of gases, vapours, mists, dusts or combustible grains, stored in a confined or semi-confined environment or volume such as a grain silo, a volume comprising a mixture of fuels, hydrocarbons or industrial dusts or of fertilizers and air, the tank of a vehicle, a driftway, etc.

TECHNICAL BACKGROUND AND PRIOR ART UNDERLYING THE INVENTION

Every year, industrial installations suffer extensive material damage, caused by fires and/or explosions. Occasionally even, this damage is accompanied by loss of life.

Efforts directed towards preventing these risks must thus be made and European Directive 1999/92/EC of 16 Dec. 1999 addresses this matter.

Mixtures of air with one or more flammable substances, defined under the term "explosive atmospheres" by European Directive 1999/92/EC of 16 Dec. 1999, may undergo explosion or ignition when they are stored at ambient or higher temperatures in confined or semi-confined environments.

Such atmospheres may be present in certain volumes such as grain silos, in the interstitial grain space, in the empty part of the storage cells above the grain, and also in the silo handling galleries in the empty "diamond" cells or intercalations or other confined spaces.

These explosive atmospheres may consist of hydrocarbons and air, of pyrolysis products and air or of aerobic or anaerobic fermentation of wet grain or of dusts arising from grain cleaning, drying or handling operations.

Other open-cast silos are also concerned since the atmosphere inside the stored mixture is explosive and can give rise to "smouldering fires" inside the stored mass or to a fire at the surface of the stored pile.

Explosive atmospheres may also be present in stocks of fertilizers, of animal or plant meals/powders, vehicle tanks, driftways, etc.

Thus, it is important to detect the risk of explosion of these explosive atmospheres.

Document WO 89/08253 describes a process and apparatus for determining whether or not a fuel can cause an explosion under the conditions present in a diesel engine. This phenomenon is studied by subjecting the fuel to exposure in the presence of a mixture of oxidizing gases while gradually increasing the temperature. In a second step, a catalytic post-oxidation reaction to $CO_2$ and water is carried out and a detector continuously measures the amount of $CO_2$ produced. The cetane number of the fuel is determined by analysing databases on a statistical model.

Similar devices are described in document WO98/18001, in which different detecting elements (sensors) are used, making it possible to determine the critical proportion of the various components in measuring chambers up to the point of forming an explosive mixture.

However, these various systems are based on a comparison relative to a reference generally determined for a specific volume and mix of fuels.

The document JP-A-09304310 describes a process for preventing the risk of spontaneous ignition in which the temperature is measured in the sample holding container and in which the critical moment is determined both on the basis of the time which has elapsed and by comparing the measured temperature with the critical temperature. The critical moment of the sample in said process is therefore not literally known.

AIMS OF THE INVENTION

The present invention aims to propose a process for anticipating and/or preventing the risk of spontaneous ignition and/or explosion of an explosive atmosphere as defined in Directive 1999/92/EC published in the JOCE L23 of Jan. 28, 2000, the fuel mix stored in a confined or semi-confined environment, for example a grain silo, an open-cast coal dust heap, a building whose atmosphere is impregnated with industrial dusts or fertilizers (bags of chemical fertilizer/ammonium nitrate) or with animal or plant powders/meals or saw dust, a tank partially filled with kerosene, petrol, hydrocarbon gases and air, etc., which would not have the uncertainties and drawbacks of the prior art processes and which can be adapted to any type of volume and to any type of fuel (in solid, liquid, emulsified, droplet or gaseous form) in the presence of air, oxygen or another oxidizing agent.

Another aim of the present invention is to propose a device which makes it possible to avoid or delay the phenomena of spontaneous ignition or explosion of such fuels stored in these confined or semi-confined environments, mixed with an oxidizing agent such as, for example, oxygen or air.

CHARACTERISTIC ELEMENTS OF THE PRESENT INVENTION

The present invention relates to a process for anticipating and/or preventing the risk of spontaneous ignition and/or explosion of an explosive atmosphere stored in a confined or packed environment, in which the temperature of the mixture is measured at the time of creation of said mixture, and the critical moment of spontaneous ignition and/or explosion of this mixture is obtained by determining the induction time, that is to say the time elapsed between the creation of said mixture and the critical moment beyond which there is a risk of said mixture spontaneously igniting and/or exploding.

The expression "explosive atmosphere" means a mixture, under atmospheric conditions, of air and of flammable substances in the form of gases, vapours, mists or combustible dusts, in which, after spontaneous ignition, the combustion is propagated throughout the unburnt mixture. If the atmosphere is homogeneous, the spontaneous ignition may take place simultaneously throughout the volume.

According to the invention, the fuel is present in solid, liquid, gaseous, mist, dust or emulsified form.

In the process of the invention, the confined environment comprising the mixture of flammable substances/air is selected from the group consisting of grain silos, centres for storing solid combustible materials such as coal dust, saw dust, fertilizers (chemical fertilizer/ammonium nitrate), animal or plant meals, driftways, fuel tanks, in particular hydrocarbon (kerosene, petroleum spirit, methane, butane, propane, etc.) tanks partially filled with air or with explosive atmospheres, optionally incorporated in a vehicle such as a truck, an aircraft, a boat, etc.

Advantageously, in the process of the invention, alarm means or means for delaying and/or preventing said spontaneous ignition and/or explosion are also used, and may be engaged automatically or, optionally, manually by the staff in charge of monitoring and handling said mixture present in the confined environment. Said means or devices must be engaged from the moment of creation of the explosive atmosphere in order to determine the critical moment of spontaneous ignition and/or explosion of the explosive atmosphere, that is to say when the time elapsed approaches the critical moment ($\tau_i$) of spontaneous ignition and/or explosion.

These various means may comprise sensors, probes, detectors, analysers or devices for diluting, separating, cooling or inertizing the mixture so as to delay or prevent said spontaneous ignition and/or said explosion.

The various elements for characterizing the critical threshold of spontaneous ignition and/or explosion of the explosive atmosphere are based on the combination of means that are well known to those skilled in the art, such as sensors, recorders, timer systems for determining the time elapsed, devices for measuring the initial temperature and variations in the temperature of the mixture over time, data integration systems such as electronic memories and chips, etc., connected to a central processing and control unit for automatically or manually actuating various alarm devices, for preventing or combating the fire, thus making it possible to prevent, delay or avoid said spontaneous ignition and/or said explosion, and also mechanisms for pumping, emptying, handling, cooling or inertizing the atmosphere at risk or flammable and combustible substances.

DESCRIPTION OF ONE EMBODIMENT OF THE INVENTION

Figure 1:
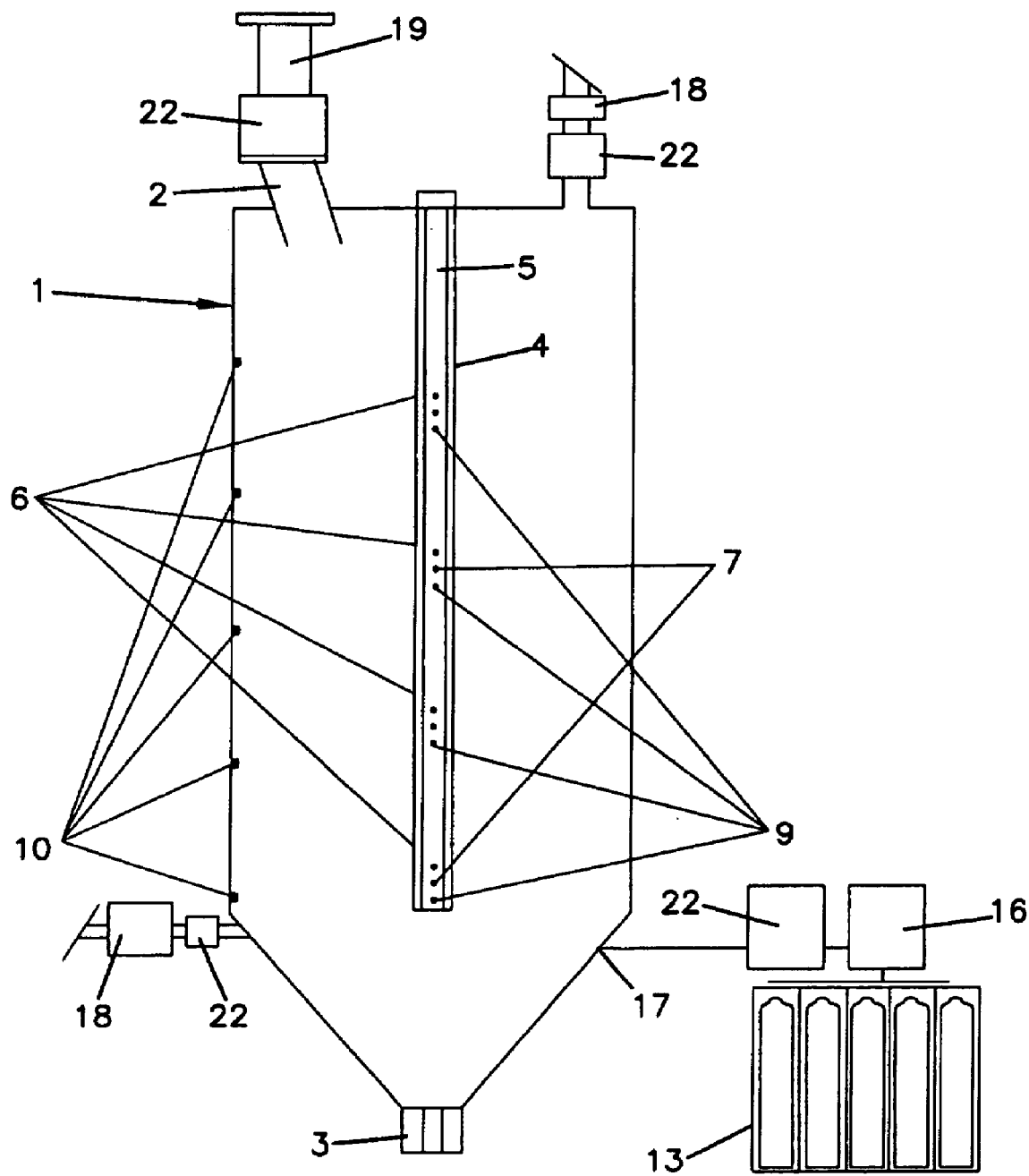
FIG. 1 shows the cell of a grain silo fitted with the device for carrying out the process according to a preferred embodiment of the invention.

According to a possible embodiment of the invention, the process for anticipating and/or preventing the risk of ignition and/or explosion concerns a vertical cell filled and emptied by gravity in a grain silo, and uses equipment as shown in FIG. 1.

The current knowledge has made it possible to identify, in silos, two main types of accident:
  fires,
  explosions,
the former occasionally being the cause of the latter.

The current state of knowledge regarding prevention and protection starts from the principle that these fires and/or explosions are caused:
  either by a self-heating of the stored products, which results in a first self-ignition, which is then propagated in the atmosphere and the products,
  or by the triggering of an explosion, usually in the handling galleries or towers, filled with flammable dusts, resulting either from a spark originating from a short-circuit on an electrical appliance or from an electrostatic discharge or a local overheating due to the friction of mechanical components.

An aim of the present invention is to use new knowledge which demonstrates that an explosive atmosphere consisting of a mixture of air, under atmospheric conditions, with flammable substances in the form of gases, vapours, mists or flammable dusts will always undergo a spontaneous ignition (see FIG. 3), even at ambient temperature, if the stored volumes are large enough for the wall effects to become negligible at the molecular impact scale. This new knowledge is moreover confirmed by the various itemized studies of self-heating and ignition of flat silos.

In the case of "dusty" atmospheres at high temperature, the induction time, that is to say the time required for the atmosphere to spontaneously ignite, may become very short and there is a risk of ignition taking place simultaneously throughout the volume of atmosphere, giving rise to a more or less violent explosion depending on the energy released (high pressures, heat) and the confinement of the atmosphere.

In this case, the preventive measures must be taken as a matter of urgency, as soon as the explosive atmosphere is created, given that the explosion and its propagation may take only a few seconds or even fractions of a second.

The inventor has chosen to illustrate this invention by its application to a conventional vertical storage cell.

The cell 1 of the silo, of cylindrical shape, comprises at the top a filling hole 2 and an emptying hole fitted with a valve 3 at the bottom.

The cell 1 is also equipped with a hollow cable 4 suspended centrally, containing an inner cable 5 in which are incorporated temperature sensors 6, generally thermocouples, humidity sensors, gas probes, etc., each spaced apart by a distance which depends on the diameter of cylindrical cell 1.

More specifically, certain parameters are measured and atmospheric samples are taken at a certain number of points inside the cell 1 by means of gas probes 7, beginning from the start of filling.

The samples are subjected to an initial analysis using an analyser 8, the analysis making it possible to introduce, in addition to the initial composition of the atmosphere and its initial temperature, other parameters such as the hygrometry and above all the time elapsed. This sampling will have to be continued either continuously or at a frequency determined by the level of risk of explosion of the atmosphere.

However, it is preferable that the monitoring of the temperature, the time elapsed and the other parameters are performed continuously by means of temperature sensors 6 and humidity sensors 9, these various sensors being placed inside the inner cable 5.

Figure 2:
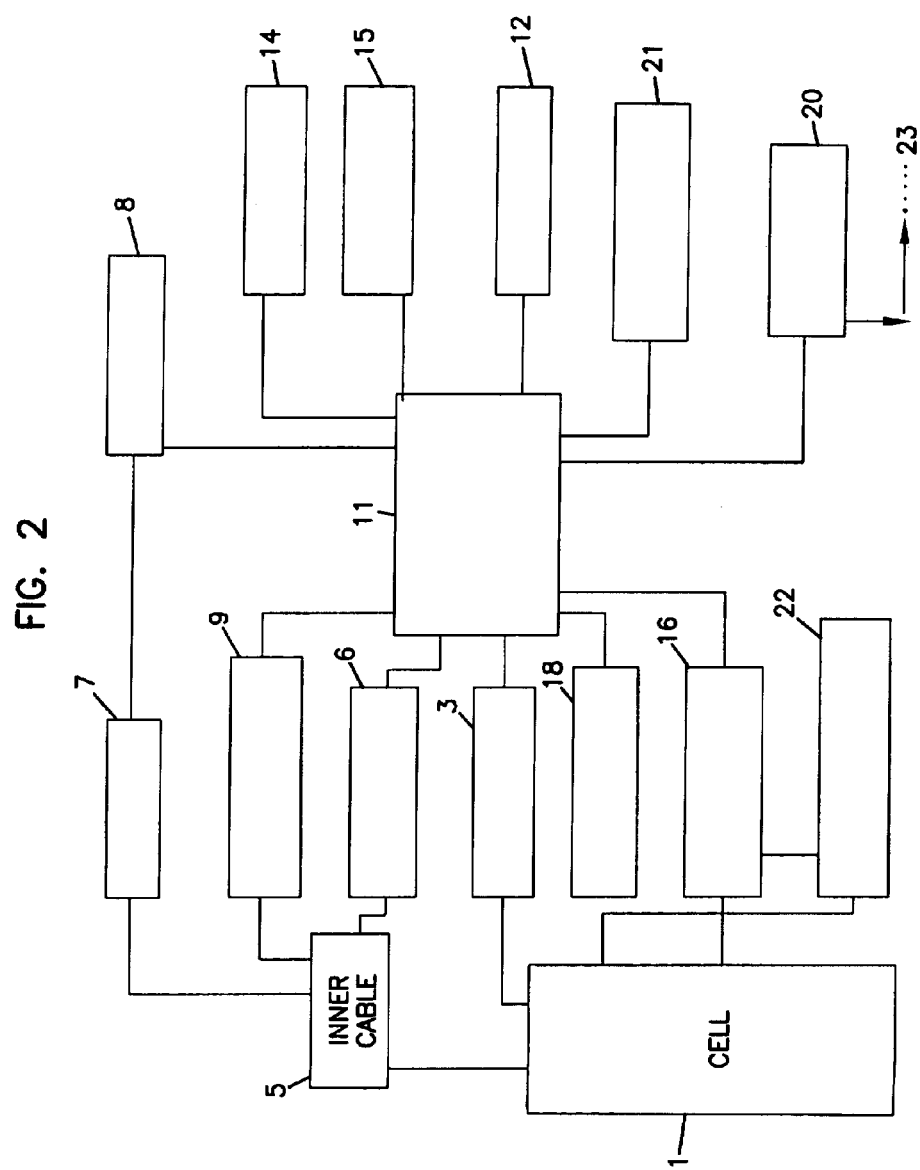
FIG. 2 shows the connections between the monitoring center and the other elements of the device for carrying out the process according to a preferred embodiment of the invention.

In practice, as soon as the flammable products to be stored with the air filling the cell 1 have been mixed together, means are employed to determine the nature of the mixture and the characteristics of the atmosphere liable to explode, both within the product and in the empty part above the stored product, as illustrated in FIG. 2.

Pressure sensors 10 are placed along the inner wall of the cell 1 so as to be able to integrate at any moment the new data into the data already stored in the control and monitoring centre 11. The monitoring centre 11 may thus control, should the need arise, the implementation of the alarm device 12 and/or device for automatic intervention via a programmer 14 and management software 15 in order to reduce and/or neutralize the risk of spontaneous ignition and/or explosion.

Advantageously, the device according to the invention also comprises a recorder 20 intended to record the data relating to the various parameters as they are acquired.

Devices 21 for varying, for example, the humidity, temperature, pressure, etc. are connected to the central processing unit 11.

In addition, the central processing unit 11 controls at output, via control systems 23 (or outputs), the silo machinery, for example the machinery associated with inter-silo transfer, emptying or filling, etc.

Among the processes for neutralizing the risk of spontaneous ignition and/or explosion, mention may be made of the inertization and suction of the atmosphere followed by storage under vacuum.

The inertization process is directed towards neutralizing the reactive nature of the atmosphere by replacing the atmosphere present in the cell 1 with a non-explosive atmosphere, for example by replacing the air (or the oxygen) with a gas such as nitrogen or carbon dioxide. The inert or inertizing gas is taken from bottles 13 as shown in FIG. 1 and then injected by means of an injection pump 16 into the cell 1 via the inlet 17.

The process for suction of the atmosphere followed by storage under vacuum or under an inert gas is itself based on the principle according to which it is the oxygen of the air, or that released by certain molecules with which it is associated, that reacts in the atmosphere and makes it explosive. During the induction period which precedes its spontaneous ignition or explosion, it is removed by means of suction pumps 18 as shown in FIG. 1 and the storage under reduced pressure or under vacuum is maintained by means of closing the shutter 19. Devices 22 for cooling the atmosphere may be used in conjunction.

The two processes may be carried out in parallel.

It is thus advantageous to include the following elements in the equipment for the vertical cell:
  suction and pumping elements for inertizing the cell at atmospheric pressure and for closing it after inertization;
  or a leaktight membrane installed inside the cell, which is open at the top so as to allow it to be filled and which is provided with a bottom hole, for example to pump the atmosphere and to place the stock under vacuum, until it is emptied out.

Figure 3:
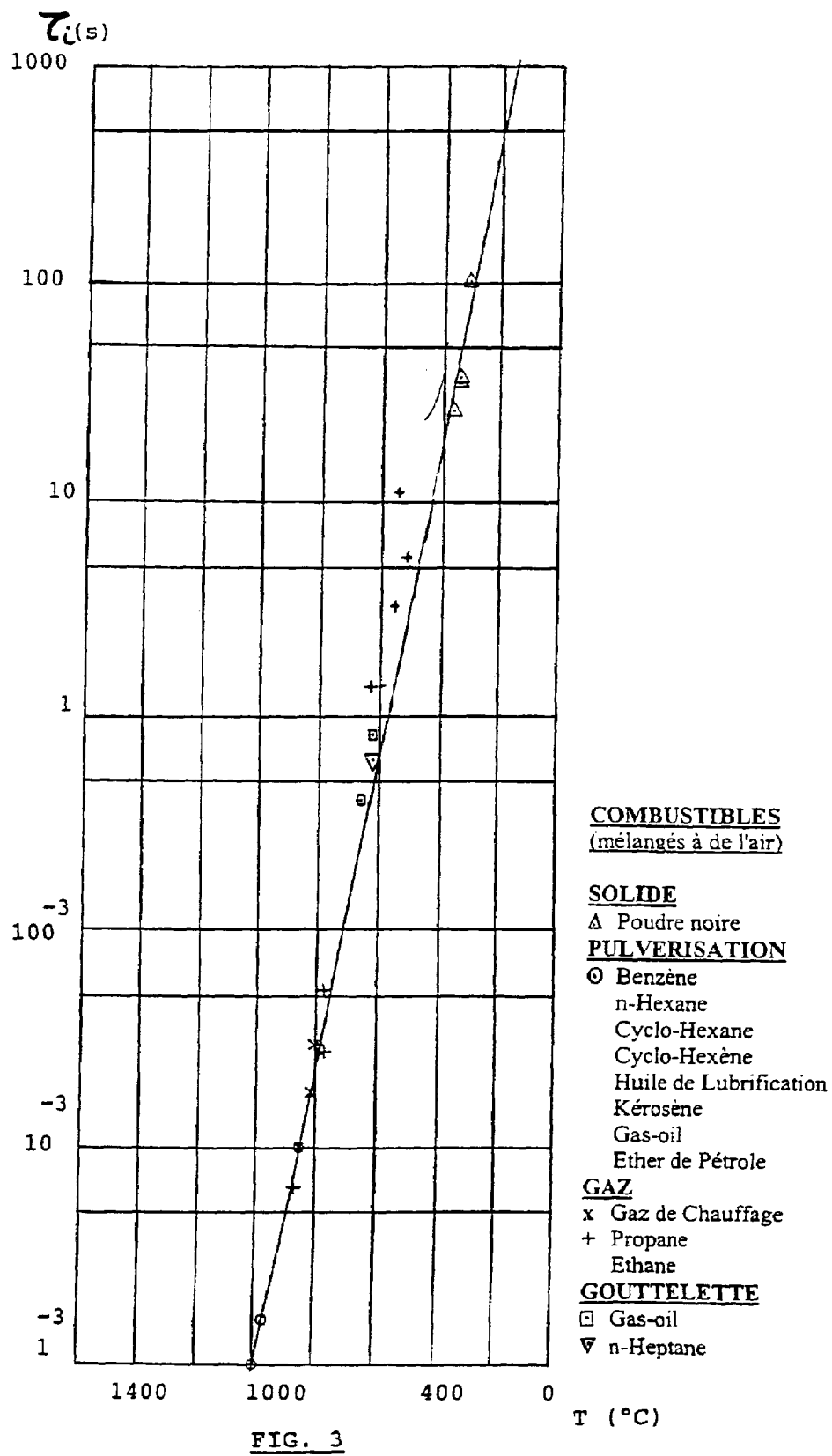
FIG. 3 shows, for different explosive atmospheres, the variations in the logarithm of the induction time $\tau_i$ a function of the initial temperature (in degrees Celsius) of said atmosphere.

FIG. 3 gives an example of experimental data which are used as reference by the monitoring centre to decide whether or not to actuate the alarm device 12 and/or the automatic intervention device via the programmer 14 and the management software 15, in order to reduce and/or neutralize the risk of spontaneous ignition and/or explosion. These data correspond to the variations in the induction time, for a fuel/oxidizing agent mixture, as a function of the initial temperature of the mixture. More specifically, FIG. 3 shows various data, acquired under constant temperature conditions, with, on the y-axis, the logarithm of the induction time, that is to say the logarithm of the time elapsed between the creation of the fuel/oxidizing agent mixture and the moment of spontaneous ignition and/or explosion, and, on the x-axis, the initial temperature of said mixture. This graph shows a curve based on the sum of various experimental data obtained with fuel mixes in solid, liquid or gaseous form, of blasting powder, benzene, cyclohexane, cyclohexene, lubricants, kerosene, propane, ethane, n-heptane, etc., in contact or mixed with air.

On the basis of these experimental data, it is possible, for a fuel/oxidizing agent mixture present in a confined environment, provided that suitable experimental techniques are complied with, to anticipate the induction time and thus the moment at which the mixture will spontaneously ignite, thus making it possible to determine the critical elapsed time threshold beyond which said fuel/oxidizing agent mixture is liable to spontaneously burst into flames and thus cause a fire and/or explosion.

As indicated in FIG. 3, it should be expected that there will be spontaneous ignition of the interstitial or peripheral atmosphere of the stored products, even though this spontaneous ignition is not preceded by a self-heating. Specifically, the curve in FIG. 3 shows the induction time of atmospheres at atmospheric pressure and at constant temperature before spontaneous ignition. Needless to say, this induction time may depend on the nature of the flammable products stored and thus on the physical or chemical change in the interstitial explosive atmosphere after mixing the products with the air contained in the cell before filling.

Legend to FIG. 3
COMBUSTIBLES→FUELS
mélanges à de l'air→mixed with air
SOLIDE→SOLID
Poudre noire→Blasting powder
PULVERISATION→SPRAYING
Benzène→Benzene
Cyclo-Hexène→Cyclohexene
Huile de lubrification→Lubricating oil
Kérosène→Kerosene
Ether de Pétrole→Petroleum ether
GAZ→GASES
Gaz de chauffage→Heating gas
GOUTTELETTE→DROPLET

What is claimed is:

1. A method for anticipating a risk of spontaneous ignition and explosion of an explosive atmosphere in an environment chosen from a group consisting of a grain silo, a center for storing coal dust, industrial dusts, animal or plant meals or chemical fertilizers or ammonium nitrates, driftways, pipe lines and storage tanks wherein benzene, cyclohexane, cyclohexene, kerosene, ethane, n-heptane, petroleum spirit, methane, butane or propane is stored in the pipes lines or the storage tanks, the method comprising;
  measuring a temperature of a mixture and any change over time from a time of creation of said atmosphere at an instant combustible vapors or gases are initially mixed or put into contact with air,
  determining a critical moment of spontaneous ignition and/or explosion of the mixture by determining an induction time remaining to go, including the time elapsed between the creation of said atmosphere and the critical moment beyond which there is a risk of said atmosphere spontaneously igniting and exploding, and
  using a means for preventing spontaneous ignition and explosion of said atmosphere when the time elapsed from the moment of creation of said atmosphere approaches the critical moment of spontaneous ignition, wherein the means is engaged manually or automatically.

2. Process for anticipating a risk of spontaneous ignition and explosion of an explosive atmosphere in an environment chosen from a group consisting of a grain silo, a center for storing coal dust, industrial dusts, animal or plant meals or chemical fertilizers or ammonium nitrates, driftways and truck, aircraft or boat tanks of hydrocarbons chosen from the group consisting of kerosene, petroleum spirit, methane, butane and propane, the method comprising:

measuring a temperature of a mixture and any change over time from a time of creation of said atmosphere, determining a critical moment of spontaneous ignition and/or explosion of the mixture by determining an induction time remaining to go, including the time elapsed between the creation of said atmosphere and the critical moment beyond which there is a risk of said atmosphere spontaneously igniting and exploding, and using a means for preventing spontaneous ignition and explosion of said atmosphere when the time elapsed from the moment of creation of said atmosphere approaches the critical moment of spontaneous ignition, wherein the means is engaged manually or automatically.

* * * * *